United States Patent [19]

Pozuelo

[11] 4,165,382

[45] * Aug. 21, 1979

[54] METHOD OF PHARMACOLOGICALLY TREATING SCHIZOPHRENIA WITH ALPHA-METHYL-PARA-TYROSINE

[76] Inventor: Jose Pozuelo, 1463 Burlington, Cleveland Heights, Ohio 44118

[*] Notice: The portion of the term of this patent subsequent to Sep. 26, 1995, has been disclaimed.

[21] Appl. No.: 842,665

[22] Filed: Oct. 17, 1977

[51] Int. Cl.² ............................................. A61K 31/195
[52] U.S. Cl. ..................................................... 424/319
[58] Field of Search ........................................ 424/319

[56] References Cited

U.S. PATENT DOCUMENTS 3,787,581  1/1974  Sandler ................................. 424/319

*Primary Examiner*—Stanley J. Friedman
*Attorney, Agent, or Firm*—Fay & Sharpe

[57] ABSTRACT

A method of pharmacologically treating schizophrenia which method comprises administering to a human being a therapeutically effective amount of alpha-methyl-para-tyrosine and an alkalinizing agent, with the alkalinizing agent being present in an amount sufficient to cause the urine of the human being to have an alkaline pH.

7 Claims, No Drawings

METHOD OF PHARMACOLOGICALLY TREATING SCHIZOPHRENIA WITH ALPHA-METHYL-PARA-TYROSINE

BACKGROUND OF THE INVENTION

The present invention relates to a method of treating patients suffering from schizophrenia and to alleviate or abolish the symptoms of the disease.

There are two major aspects to consider in the schizophrenic patient: (1) a disturbance of mood and affect and disorganization of the thinking process, and (2) the hallucinations and delusions which render the individual uncapable of dealing effectively with the motivations and decisions of every day living.

The biochemical basis of the schizophrenia has been suspected for a long time and the identification of the biochemically altered factors, be they genetically induced or triggered by environmental situations, enzymatic or electrolytic in nature, etc., have been the object of numerous investigations. Even if the etiological agent of all these disturbances is unknown, an abnormality in the mechanism of the neurotransmitters is evidently involved. It is well known that the catecholamines, specifically dopamine and noradrenaline are two fundamental neurotransmitters and it has been speculated that an alteration in the synthesis, release, catabolism or re-uptake of these compounds could be responsible for the symptoms of schizophrenia. Heretofore to accomplish this certain therapeutic agents have been utilized. These agents are the so-called neuroleptics (e.g., chlorpromazine, thioridazine, haloperidol, etc.).

The alpha-methyl-para-tyrosine is known to have an affect on the enzyme tyrosine hydroxylase which regulates the synthesis of dopamine and noradrenaline, thereby being responsible for the amount of their by-products, which otherwise create a feed-back mechanism which influences the enzyme tyrosine hydroxylase. However, it was well known that treatment with alpha-methyl-para-tyrosine resulted in crystalluria. Accordingly, while alpha-methyl-para-tyrosine created the desired effect, it could not be used on human beings.

Accordingly, the main object of the present invention is to provide a method of treating schizophrenia using alpha-methyl-para-tyrosine in therapeutic doses without the formation of alpha-methyl-para-tyrosine crystals in the patient's urine.

Other objectives will be apparent to those skilled in the art from a reading of the following description and claims.

SUMMARY OF THE INVENTION

The present invention provides a safe and effective method of treatment of schizophrenia by abolishing the cumbersome symptoms that prevent the patient from functioning normally. Broadly, this is accomplished by administering to the schizophrenic patient a therapeutically effective dose of the potent neuroleptic, alpha-methyl-para-tyrosine (something referred to herein as AMPT) and an alkalinizing agent, with the alkalinizing agent being present in an amount sufficient to cause the urine of the person being treated to have an alkaline pH, preferably in excess of about 7.4.

In another aspect, the present invention concerns a pharamceutical composition which is used in the practice of the foregoing method. This composition comprises a mixture of alpha-methyl-para-tyrosine and an alkalinizing agent.

A still further object of the invention is to provide a method of treating a human being with alpha-methyl-para-tyrosine while avoiding alpha-methyl-para-tyrosine crystalluria.

DESCRIPTION OF THE PREFERRED EMBODIMENTS OF THE INVENTION

The present invention concerns the use of alpha-methyl-para-tyrosine ($C_{10}H_{13}NO_3$) in the treatment of schizophrenia. This compound is sometimes herein identified as AMT. It has the following structural formula:

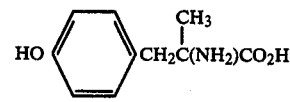

In the practice of the present invention alpha-methyl-para-tyrosine is administered in an therapeutic amount (in therapeutic doses). That is, the person being treated is given increasing amounts of the concerned compound until the symptoms of schizophrenia are controlled and are no longer observed. The exact amount to be utilized may vary from a patient to another, and the most appropriate dosage must be determined emperically. However, in practice, alpha-methyl-para-tyrosine has been administered in amounts of 10–12 gm. per day, divided in four doses, to control the florid symptoms and in a maintenance dose of 4–6 gm. per day, to prevent relapse.

The alkalinizing agent can be any one of the many materials used to alkalinize urine. Such materials include, but are not limited to, sodium bicarbonate, ammonium chloride, and the like. An alkalinizing agent which is especially effective is a commercially available product known as Polycitra, manufactured by Willen Drug Company. This product contains 30 grains of citric acid, 45 grains of sodium citrate and 50 grains of potassium citrate for every 30 ml of syrup base solution.

The exact amount of alkalinizing agent to be utilized varies from person to person and the diet the individual receives. All that is required is that sufficient alkalinizer be utilized to render the urine of the person being treated basic. However, it is preferred that the pH of the urine of the person being treated must be greater than about 7.4 in order to prevent alpha-methyl-para-tyrosine crystalluria. In practice, it has been determined that it is most desirable to use enough alkalinizer to cause the urine of the person being treated to exhibit a pH of about 7.8 to 8.0 (ideal).

The alpha-methyl-para-tyrosine can be administered in various ways. For example, it can be given in pill or capsule form, in powder form mixed with marmalade or other foods, with or without a filler, alone or mixed with the alkalinizing agent. If desired, the alpha-methyl-para-tyrosine can be administered intravenously. In such a case, it is convenient to dissolve the alpha-methyl-para-tyrosine in a basic solvent. This is readily accomplished by mixing the powdered compound with a buffer phosphate solution (500 mg of AMPT in 10 ml buffer phosphate) and dissolving it at a pH of 11.5 by adding NaOH and bringing the pH to 7.4 to 8 with HCl solution. The compound solution is then diluted further in sterile water to obtain 500 ml of solution, correcting the final pH to 7.4.

As above noted, the alpha-methyl-para-tyrosine, the alkalinizing agent or the combination thereof can be mixed with other materials. For example, in the case of a tablet, the composition can also include fillers, binders, and diluents such as lactose, methylcellulose, talc, gum tragancanth, gum acacia, agar, polyvinylpyrrolidone, calcium stearate, and/or corn starch, etc. In the case of a liquid solution or suspension for oral administration, the composition can include a filler such as sodium carboxymethylcellulose and/or syrup, e.g., a glycerine based syrup. In the case of a parenteral solution or suspension, the composition will comprise a suitable solvent or other liquid such as a saline solution.

The practice of the present invention is further exemplified by the following general discussion and case studies.

The patients, with well documented histories of schizophrenia were persuaded to accept treatment, without court order, with the consent and encouragement of their families, as previous treatments have been unsuccessful to accomplish more than a moderate recovery after intense treatments, with relapse after a short term, the patients having never gained full insight into the nature of their illnesses. All patients had severe and diagnostically unmistakable symptoms of schizophrenia and the treatment results demonstrated effectiveness of the present invention. Patients were hospitalized voluntarily and underwent a complete physical examination, routine blood tests and urinalysis, all within normal limits, except for some minor alterations of liver function in one patient. A period of four days was used for each patient before starting treatment with alpha-methyl-para-tyrosine, in order to determine the amount of alkalinizing agent (Polycitra) needed to obtain a urinary pH close to 8 and to observe patient's behavior, in all cases was found to be definitively schizophrenic.

Doses of AMPT were started in an amount of 3-4 grams per day, divided in four doses, and increased gradually by 0.5 gm/day up to 10-12 gm daily as total dose.

The tentative doses of the alkalinizer Polycitra to obtain a urinary pH close to 8 were determined empirically in each case as needed to maintain the desired pH.

Urine specimens were checked four times daily to determine the urinary pH and to look if any crystals of AMPT would appear in the sediment. Routine blood test, liver function tests and kidney studies were done weekly to check if the treatment would cause any alteration.

When the dosage of AMPT, administered orally, was around 10 gm. per day the patients started to show an almost dramatic improvement which persisted when administered a much lower dose of AMPT as a maintenance treatment. Changes obtained in patients treated according to the practice of the present invention are illustrated in the following reports.

CASE REPORTS

Case 1

The patient was a 30 year old single, white male, who for about the last 10 years exhibited a strange behavioral pattern feeling that people were persecuting him, that he was being followed in the street and that his family was trying "to catch him in something wrong" in order to put him in jail so that he would not give them more trouble. He had been seen by a psychiatrist and treated as an outpatient with heavy doses of Thorazine (up to 200 mg. q.i.d.) for two months but as the same ideas persisted he had to be hospitalized and treated with electroconvulsive therapy (ECT), receiving a total of 14 ECT treatments with relative improvement. However, two months later he started to voice the same type of ideas and had to be hospitalized again for a period of three months, being treated with Mellaril, Stelazine. As he did not respond to these psychotropic medications, he was given ECT treatments again. After being discharged from the hospital he was maintained on Thorazine 200 mg. q.i.d. He, under this medication, did not voice his ideas openly any longer but he was afraid of remaining at home and had to be moved to live with relatives, having very few contacts with his parents, brothers and sisters. He continued seeing a psychiatrist as an outpatient on the average of once a month and changed from one medication to another without having any significant improvement or being unable to hold a job. In 1970 he was hospitalized again in another private institution where he was treated with different phenothiazines and individual and group psychotherapy for a period of six months, being released to the care of his uncle as still he maintained the same delusions and the convivence with his parents was impossible. After two months he was hospitalized again and as his delusions persisted, treated with 10 ECT treatments and released on Thorazine 100 mg. t.i.d. and Stelazine 5 mg. t.i.d. However, he continued being unable to find or look for a job, had gained a lot of weight, had become very sloppy and unkempt in his appearance, against his previous background of neatness. In the Spring of 1973 he ran way from his uncle's home and during 10 days he remained in hiding, living on a very low budget and spending the money he had taken from his uncle. He was found by police, hospitalized in another private institution where he was treated with different psychotropics and received a total of 20 ECTs in the course of three months, being discharged on no medication. Two months later he started to express overtly at the same time delusions of being persecuted, of being followed in the street and of his family disliking him. In November 1973 he had to be hospitalized again for a period of two months receiving insulin treatments and a brief course of ECT on alternate dates with the insulin comas. With this treatment he had significant improvement and for the first time he seemed to forget completely about his delusions without mentioning them after being released from the hospital. He continued on a maintenance treatment of Thorazine 100 mg. t.i.d. However, he was very aloof, unmotivated to look for a job or to do anything, including exercise, for which he had become 25 kilograms overweight, depressed and refused to live at home or to have contact with his parents.

During the following two years he was treated as an outpatient with different medications which included Stelazine, Surmontil, Prolixin, Haldol and Mellaril, which although controlling his delusions to the point of not being voiced overtly, never blocked them completely, as he remained withdrawn and isolated from family, without friends and unmotivated to do anything. He complained of lack of initiative, no interest in doing anything and lacking power of concentration when it was suggested that he start some kind of work or studies. Although encouraged to find a job, or to work in the family business, he refused to undertake such activities. After many arguments with his family and a lot of persuasion used by his psychiatrist he was convinced to start working in an office. He attended one day, however, the second day he left work without letting his family or employer know where he was. He was found by friends living in a cheap boarding house and returned by them to live with his uncle.

While still maintained on the medications mentioned he continued to voice his old delusions, becoming more withdrawn for which, after a short hospitalization and a brief course of ECT, he had to be hospitalized again in November, 1975 and given a course of 14 ECTs in a period of two months, being discharged on Jan. 6, 1976. After discharge he continued being treated with Prolixin IM, 25 mg. monthly, Stelazine 5 mg. t.i.d. and Mellaril 200 mg. h.s. He continued unmotivated to work, keeping underneath his paranoid ideas and isolated from people.

In July 1976, he was evaluated by two psychiatrists who confirmed a diagnosis of paranoid schizophrenia, which he had been given by previous psychiatrists from different hospitalizations. Although very reluctant at first, he was persuaded to start treatment with alpha-methyl-para-tyrosine and remained as an inpatient during the duration of the treatment for a period of six weeks. His Prolixin shots had been discontinued two months before hospitalization and the Mellaril and Stelazine two weeks before admission to the hospital.

After initial physical evaluation did not reveal any contraindication to treatment, he was started on alpha-methyl-para-tyrosine, receiving initially 3 g. per day, divided in four doses. The doses were increased gradually to the rhythm of ½ a gram a day to a maximum of 11 grams a day, divided in four doses. At the same time as given alpha-methyl-para-tyrosine, he was administered Polycitra orally to obtain a urinary pH of 7.5–8. When the doses of alpha-methyl-para-tyrosine reached a daily amount of 10 g. per day the patient started to show a significant improvement, acting more normal and reaching a degree of improvement that, according to his family, "had never been seen in the last 10 years." He gained insight almost suddenly into his condition, stating that the ideas of being persecuted, being followed in the streets and his family wanting to put him in jail were "crazy ideas," realizing that he had been affected by mental illness for a long time and that now his major problem would be to get a job and to catch up with all the time he had lost. Doses of alpha-methyl-para-tyrosine of 11 gm. per day were maintained with proper alkalinization of the urine to a pH of 7.5–8 by administering 2 tablespoons of Polycitra four times a day, during one month, after which the doses of AMPT were reduced ½ a gram a day to a maintenance dose level of 4 gm. of AMPT daily and alkalinization of urine with Polycitra, 1 tablespoon after each meal. The doses of AMPT continued to be given four times a day and given in the form of powder, 1 gram each time mixed with jelly or marmalade.

The treatment with alpha-methyl-para-tyrosine in the dose of 4 gm. per day was maintained during three months at which time the patient had already started to work in the family business, remaining at home without any problems and stating that he was feeling as never before. The alpha-methyl-para-tyrosine was discontinued on Dec. 20, 1976, with patient continuing doing well, working in the family business and without any evidence of paranoid ideas or altered mood until the beginning of February, 1977, which was seven months after he had been discharged from the hospital. It was noticed by his family at that time that he was becoming somewhat withdrawn, starting to be isolated from family and friends and although he did not voice openly his delusions when questioned by his psychiatrist he manifested his old fears and same delusions, although bothering him to a lesser degree. Because of the lack of experience in the use of chronic administration of AMPT it was advised treatment with other neurleptics and recommended treatment with Prolixin 25 mg. IM monthly, Thorazine 300 mg. h.s. and Cogentin 2 mg. h.s., which he accepted without any reluctance. However, although living at home he continued to maintain his delusional ideas and on May 22nd he disappeared from home, did not report at work and two weeks later he was found in a vacation resort, living in an inexpensive hotel remaining in his room almost all the time, barricading the door, behavior that made the owner suspicious and caused him to notify the police. He was hospitalized on June 14th and treated with Haldol 10 mg. q.i.d., Cogentin 2 mg. h.s., without these medications having removed his delusions after one month of treatment. Therefore, his family requested treatment with AMPT again.

Doses of AMPT, with proper alkalinization with Polycitra, were started at an initial dose of 8 gm. per day and increased one gram daily to 11 gm. per day, given in four divided doses. After 10 days of treatment the patient's delusions had disappeared completely, gained full insight about his conditions and expressing disgust and frustration about his "crazy ideas," pleading not to have his AMPT treatment discontinued.

Doses of AMPT were reduced to a maintenance dose of 5 mg. per day with proper alkalinizaton of the urine with Polycitra, and the patient continues on this dose without any evidence of delusions or thought disturbance until the present.

Case 2

The patient is 25 years old, single, white female, who in 1971 had to quit college because of inability to concentrate, misinterpretation of what she was reading and the belief that people were laughing at her and knew all her life. She isolated herself in her room without communication with the other female students in her dorm and was found staring for hours, this being interrupted by giggling and laughing for no reason. Therefore, her parents were notified and she was taken to a psychiatrist who diagonosed her of schizophrenia, hebephrenic type. She was treated with Haloperidol up to 60 mg. per day, responding to some degree to treatment in the sense that she was not mentioning her delusions but remaining secretive, withdrawn and unable to concentrate and to continue her studies the following fall. She gained a lot of weight (between 40–50 pounds) and her appearance became very sloppy about what she looked unconcerned. During the year 1972–73 she continued to be treated as an outpatient, with monthly visits to a psychiatrist, who alternated different medications without being able to alter her withdrawn behavior and lack of motivation to do anything. Toward the end of Spring 1973 she had cut herself from all relations with her girlfriends and initiated a very promiscuous heterosexual relation, unconcerned about the consequences and very much against what had been her previous prudish behavior. She started to express the feeling that people didn't like her, that they knew what she was thinking and that they were looking at her and criticizing her for no reason. In the Fall of 1973 she had to be hospitalized because her behavior had become extremely disturbed, had delusions about people thinking she was homosexual, refused to go out of her room where she spent most of the time staring through the window or writing, what apparently was not making any sense, in a book, which she always kept locked. She was hospitalized for three months and in view of the lack of response to heavy doses of phenothiazines (Thorazine, Mellaril, Stelazine, Trilafon and Surmontil, combined with other neuroleptics), she was given a course of 14 electroconvulsive treatments (ECT), with significant, although temporary improvement. She continued as an outpatient maintained on heavy medication but still with the same delusions and unable to restart her studies or willing to look for any job.

In June 1974 she had to be hospitalized again for three months, treated with different neuroleptics, given a course of 8 electroshocks which resulted in a moderate degree of improvement and discharged from the hospital. In February 1975 she had to be hospitalized again because her behavior had become rather aggressive, directing a lot of hate toward her mother and making convivence impossible at home. She was given a course of insulin comas and a brief course of ECT resulting in temporary improvement. However, during the Fall she had to be hospitalized again because of her continuous quarreling with other members of the family and tremendous hate towards her mother. She remained hospitalized and was treated with different phenothiazines until February 1976 at which time her behavior had not changed to the point of being possible to send her home. After several attempts to send her to live with some relatives willing to accept her failed, she was committed to a state hospital. She remained hospitalized until March 1977, having worked in a rehabilitation program and being assigned to a factory nearby where she worked as a weaver. However, after two weeks she quit her job and ran away, being found in a distant city, living on a low budget pension and involved again in promiscuous relations.

Without much difficulty on her part and the consent of her parents on Aug. 7, 1977, she was hospitalized to be treated with alpha-methyl-para-tyrosine, after discontinuing her last medications (Haldol 10 mg. q.i.d., Mellaril 200 mg. h.s. and Akineton retarde 5 mg. b.i.d.).

Doses of alpha-methyl-para-tyrosine were started at 6 gm per day, divided into three doses and increased gradually to 10 mg. a day, divided in four doses, administered in powder form, mixed with granulated sugar. Meanwhile, the urine was alkalinized to a pH close to 8 by giving Polycitra 2 tbsps. q.i.d.

The patient started to improve very significantly four days after maintained on a dosage of alpha-methyl-para-tyrosine of 10 gm. per day, becoming aware of her condition, apologizing to her parents for all the troubles she had created for them and openly stating that she did not doubt she had had severe mental illness. Doses of alpha-methyl-para-tyrosine were maintained at a level of 10 gm per day during 20 days and reduced gradually to a maintenance dose of 4 gm per day divided in four doses. The patient, who still is maintained on alpha-methyl-para-tyrosine, states that she never felt so well and asked to be maintained on the same treatment. She had initiated work in the family store and according to her family is doing satisfactorily.

Case 3

The patient is 20 years old, single, white male, student, who quit the first year of college in May 1975 as, although in high school had been an excellent student, he had started to fail his examinations, because of lack of concentration and difficulty to understand and assimilate what he read. Otherwise, he was sleeping very poorly and to present a staring look which made his family suspicious of him being mentally ill.

The information from his family was that he had started to act strange about April of 1975, becoming withdrawn, uncommunicative, behavior that was at first attributed by his family to the fact that his girlfriend had dropped him. However, his girlfriend stated that she had stopped dating him because he was behaving in a very unusual way. In August 1975 his behavior had become very bizarre, staring through the window, looking into space and remaining in his room for hours without talking or doing anything. At the insistence of his family he was seen by a psychiatrist who prescribed Mellaril 100 mg. t.i.d. without any significant change in his behavior, except for him starting to verbalize his ideas that "the important thing in life was love, people didn't understand him and could not believe that he had telepathy and was able to influence people about becoming sad if he wanted them to be sad and happy if he wanted them to be happy, not needing for that to have any contact with them." He stated he was going to write a book that would become a best seller because it was about the new discovery that he only knew. In September 1976 he became very withdrawn, irritable, and still voicing his delusions to some friends. In November 1976 he disappeared from home and was found two days later by police walking in the street, half naked and reluctant to answer questions. He was hospitalized the same day and treated with electroconvulsive therapy, receiving 12 ECTs in the course of six weeks and discharged on Mellaril 400 mg. a day. One month later he started to evidence the same type of delusions he had had before, although apparently being more disorganized in his thinking and articulating more his delusional ideas. His psychiatrist started to treat him with Tofranil 100 mg. daily, Mellaril 100 mg. q.i.d. and Akineton 5 mg. b.i.d. However, he continued to have the same delusional ideas about telepathy and influencing people and as his delusions became more pronounced and he became more argumentative and difficult to deal with him at home, he was hospitalized again and treated with Haloperidol 10 mg. t.i.d., Akineton 5 mg. t.i.d. and the same dose of Tofranil, without any significant improvement or change in his delusional thinking. In May 1977, his medication was changed to Prolixin Decanoate 25 mg. every two weeks, Thorazine 100 mg. a day, Stelazine 5 mg. b.i.d., medication that was able to stop him from voicing his delusions but not to abolish them. However, he became more uncommunicative and withdrawn, unable to maintain his concentration or to do any studying. Medications were continued without any significant improvement until July 1977 at which time his medications were discontinued and he was persuaded but most reluctant to accept treatment with alpha-methyl-para-tyrosine.

A starting dose of AMPT was of 4 gm per day, divided in four doses, which was increased ½ gm per day up to 10 gm per day, in four divided doses. Meanwhile, his urine was maintained to a pH about 7.5 by administration of Polycitra, 1½ tablespoons, four times a day.

One week after being maintained on alpha-methyl-para-tyrosine (10 gm daily) an almost dramatic improvement was noticed by his family. He delusions disappeared completely and his family stated that his mood, relation and affection to them and to his brothers and sisters became as normal as it was three years before. The alpha-methyl-para-tyrosine was maintained to a dosage of 10 gm daily during 20 days and gradually decreased to 5 gm a day, which still is maintained at present because his family is very much afraid that he could relapse to his former condition. Alkalinization of the urine was maintained with a tablespoon of Polycitra three times a day.

IN SUMMARY

Treatment with AMPT demonstrated in three patients that a dramatic improvement, with disappearance of their mental disturbances (including affect, thought and delusional ideas), gaining total insight into the nature of their illness with the degree of recovery never accomplished before with other neuroleptics. None of the patients had crystalluria in the daily urine specimens and the side effects were significant. A moderate degree of drowsiness observed after a few days of treatment with AMPT disappeared later when the doses started to be decreased and hypotension which occurred in all three patients in the range of 20–30 mm Hg neither bothered the patient nor was reason to alter the dosage.

The results and information set forth above indicate that alpha-methyl-para-tyrosine is effective in the treatment of schizophrenia with advantage over previous existing treatments. The use of AMPT demonstrated its control of the florid symptoms of schizophrenia and prevented relapse while the patient was administered a maintenance dose in the range of 4–6 gm per day. The fact that these three patients did not receive any other medication while receiving AMPT, other than the alkalinizer Polycitra and gained total insight into the nature of the illness which had incapacitated them lends unequivocal support to the effectiveness of AMPT in the treatment of schizophrenia.

The effects of alpha-methyl-para-tyrosine are thought to be due, in the main, to the inhibition of the tyrosine hydroxylase enzyme, with consequence decrease of catecholamines and their byproducts and self-regulation of the proper synthesis through a feed-back mechanism. However, the present invention is not necessarily directed to this mechanism but to a means to treat the schizophrenia with a compound (AMPT) with proved advantage over other treatments available.

One additional aspect of the present invention is the provision of a means for using alpha-methyl-para-tyrosine in human beings without experiencing crystalluria, regardless of the condition being treated. As before noted in detail, this is accomplished by concurrently administering to the person taking AMPT a sufficient amount of alkalinizer to cause the patient's urine to be basic, preferably with a pH above 7.4.

Otherwise, in regard to the alkalinizing method mentioned, it is to be noted that by using the broad concept of the present invention it is possible to treat mental patients suffering from other conditions, e.g., manic psychosis, with alpha-methyl-para-tyrosine.

In the practice of the invention, it is preferred to use AMPT, however, methyl esters of AMPT may also be employed provided such compounds inhibit the tyrosine hydroxylase enzyme with consequent decrease in the presence of catecholamines. Best results are obtained when the racemic (dl) or levorotatory (l) forms of AMPT are used. The dextrorotatory (d) form of AMPT can also be used, but it is less effective than either the racemic or levorotatory forms.

While there have been described what are at present considered to be the preferred embodiments of this invention, it will be obvious to those skilled in the art that various changes and modifications may be made therein without departing from the invention, and it is, therefore, aimed in the appended claims to cover all such changes and modifications as fall within the true spirit and scope of the invention.

What is claimed is:

1. A pharmacological method of treating schizophrenia in human beings with alpha-methyl-para-tyrosine without causing the formation of alpha-methyl-para-tyrosine crystalluria said method comprising:
   administering to a schizophrenic human being a therapeutically effective amount of alpha-methyl-para-tyrosine and an alkalinizing agent, said alkalinizing agent being present in an amount sufficient to cause the urine of said human being to have an alkaline pH.

2. The method of claim 1 wherein alkalinizing agent is present in an amount sufficient to cause the pH of said urine to be in excess of about 7.4.

3. The method of claim 2 wherein alkalinizing agent is used in an amount sufficient to cause the pH of said urine to range from about 7.8 to 8.0.

4. The method of claim 1 wherein said alkalinizing agent is selected from the group consisting of sodium bicarbonate, ammonium chloride and mixtures thereof.

5. The method of claim 1 wherein said alkalinizing agent is a mixture of citric acid, sodium citrate and potassium citrate.

6. The method of claim 1 wherein said alpha-methyl-para-tyrosine, is administered in an amount ranging from 3 to about 14 gm per day.

7. The method of claim 1 wherein either the racemic or levorotatory form of alpha-methyl-para-tyrosine is used.

* * * * *